United States Patent
Goad et al.

(10) Patent No.: US 9,724,724 B2
(45) Date of Patent: Aug. 8, 2017

(54) SUBSTANCE APPLICATOR HAVING A CONTROLLABLE SUBSTANCE FLOWRATE

(71) Applicant: EIRAS MEDICAL LLC, Atlanta, GA (US)

(72) Inventors: T. Bradley Miner Goad, Atlanta, GA (US); Bjoern Niklas Jemsby, Atlanta, GA (US); Miles Graivier, Atlanta, GA (US)

(73) Assignee: Eiras Medical LLC, Atlanta, GA (US)

( * ) Notice: Subject to any disclaimer, the term of this patent is extended or adjusted under 35 U.S.C. 154(b) by 42 days.

(21) Appl. No.: 14/660,563

(22) Filed: Mar. 17, 2015

(65) Prior Publication Data

US 2015/0258568 A1 Sep. 17, 2015

Related U.S. Application Data

(60) Provisional application No. 61/954,119, filed on Mar. 17, 2014.

(51) Int. Cl.
*B43K 5/14* (2006.01)
*B05C 17/005* (2006.01)
(Continued)

(52) U.S. Cl.
CPC ............ *B05C 17/005* (2013.01); *A47L 13/17* (2013.01); *A61M 35/003* (2013.01);
(Continued)

(58) Field of Classification Search
CPC ..... A61M 35/006; B05C 17/005; A45D 37/00
(Continued)

(56) References Cited

U.S. PATENT DOCUMENTS

| 3,369,267 A | 2/1968 | Friedland et al. |
| 4,084,910 A | 4/1978 | LaRosa |

(Continued)

FOREIGN PATENT DOCUMENTS

| EP | 0109737 A2 | 5/1984 |
| WO | WO 2007/130982 A2 | 11/2007 |

OTHER PUBLICATIONS

Tapemark, "Snap!® and Snapplicator™ Packaging from Tapemark Dispenses Unit-doses", retrieved from http://www.tapemark.com/snap.html, on Jul. 22, 2015.

(Continued)

*Primary Examiner* — Jennifer C Chiang
(74) *Attorney, Agent, or Firm* — Alston & Bird LLP

(57) ABSTRACT

Various embodiments are directed to an applicator for dispensing a substance according to a desired flow rate. The applicator comprises a flexible card, a substance reservoir attached thereto, and an applicator head secured to the flexible card opposite the substance reservoir. The applicator head comprises a plurality of pores that, when secured to the flexible card, are compressed. In various embodiments, the pores are compressed by physical compression and/or by annealing. Upon flexing the flexible card along a score line, the substance reservoir ruptures and the substance is directed into the applicator head. Upon introduction of the substance to the applicator head, the pores of the applicator head expand and the substance is directed to an applicator surface of the applicator head.

17 Claims, 14 Drawing Sheets

(51) Int. Cl.
  *A61F 13/40* (2006.01)
  *A61M 35/00* (2006.01)
  *B65D 75/30* (2006.01)
  *B65D 75/58* (2006.01)
  *A47L 13/17* (2006.01)
  *A45D 37/00* (2006.01)
  *A61B 17/20* (2006.01)

(52) U.S. Cl.
  CPC .......... *A61M 35/006* (2013.01); *B65D 75/30* (2013.01); *B65D 75/585* (2013.01); *A45D 37/00* (2013.01); *A45D 2200/1036* (2013.01); *A61B 17/20* (2013.01)

(58) Field of Classification Search
  USPC .................................................. 401/132–134
  See application file for complete search history.

(56) References Cited

U.S. PATENT DOCUMENTS

| | | | |
|---|---|---|---|
| 4,140,409 A | | 2/1979 | DeVries |
| 4,430,013 A | | 2/1984 | Kaufman |
| 4,493,574 A | | 1/1985 | Redmond et al. |
| 5,308,180 A | * | 5/1994 | Pournoor .............. A45D 34/04 401/132 |
| 5,316,400 A | | 5/1994 | Hoyt et al. |
| 5,538,353 A | | 7/1996 | DeHavilland |
| 5,791,801 A | * | 8/1998 | Miller ................ A61M 35/003 401/132 |
| 6,422,778 B2 | | 7/2002 | Baumann et al. |
| 6,536,975 B1 | | 3/2003 | Tufts |
| 6,991,393 B2 | | 1/2006 | Tufts et al. |
| 7,121,409 B1 | | 10/2006 | Hamilton et al. |
| 7,241,065 B2 | | 7/2007 | Tufts et al. |
| 7,422,388 B2 | | 9/2008 | Tufts et al. |
| 7,506,762 B2 | | 3/2009 | Nelson et al. |
| 8,388,248 B2 | * | 3/2013 | Jemsby ............... A61M 35/003 401/132 |
| 2005/0047846 A1 | | 3/2005 | Narang et al. |
| 2006/0283727 A1 | | 12/2006 | Nelson et al. |
| 2010/0166485 A1 | | 7/2010 | Jemsby et al. |

OTHER PUBLICATIONS

International Searching Authority, International Search Report and Written Opinion for International Application No. PCT/US2015/021081, Jun. 22, 2015, 14 pages, European Patent Office, The Netherlands.

* cited by examiner

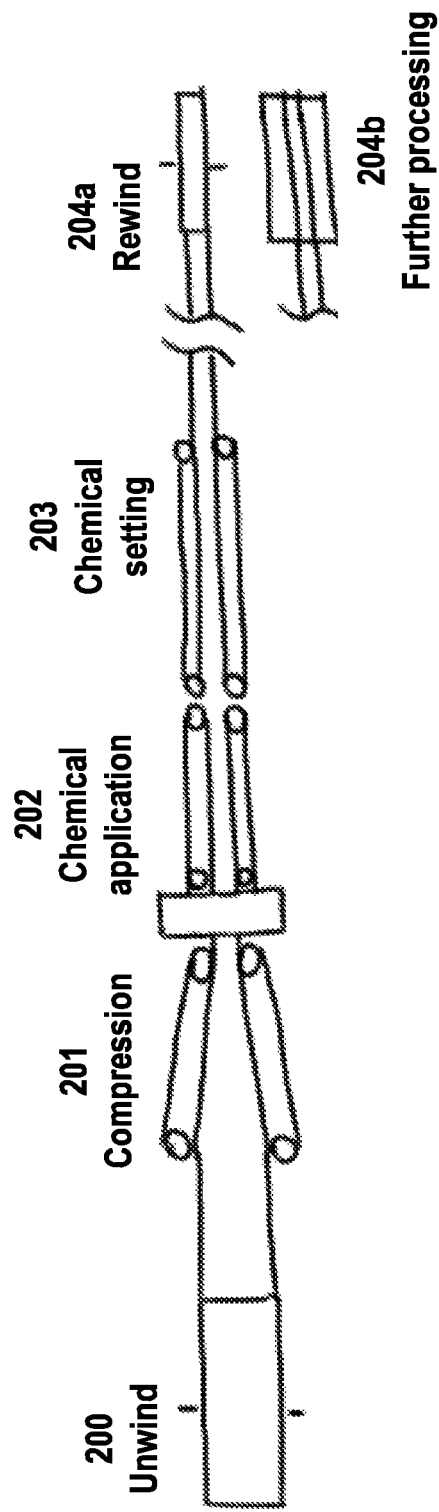

SUBSTANCE APPLICATOR HAVING A CONTROLLABLE SUBSTANCE FLOWRATE

CROSS-REFERENCE TO RELATED APPLICATIONS

This patent application claims priority from U.S. Provisional Application Ser. No. 61/954,119, filed Mar. 17, 2014, which is incorporated herein by reference in its entirety.

TECHNICAL FIELD

Various embodiments relate to the field of applying fluids, fine powders, and other substances to a surface from a reservoir.

BACKGROUND

Disposable applicators are generally considered to be economical for dispensing small quantities of liquids and other substances such as, for example, hand sanitizer before being discarded after a single use. However, these applicators are generally designed for dispensing small quantities of liquids. Typical amounts of liquid are less than 1 milliliter. Utilizing similar designs for larger quantities of substance may provide non-uniform application of the substance, or may result in over-saturating a felt, cotton, sponge, or other applicator head. For example, in some designs large volumes of liquids may gush or over-saturate an applicator head causing waste or difficulty in accurately dispensing and applying a uniform quantity of liquid. Moreover, larger foam or swab applicator heads can become distorted and compressed during the folding typically needed to activate the disposable applicator. Distorted or compressed applicator heads may reduce the amount of liquid dispensing, reduce the control over the rate and uniformity of liquid dispensing and have a negative impact on liquid distribution. Additionally, this distortion or compression can result in a less flexible applicator head material surface and a reduced ability of the applicator head to absorb and temporarily store fluid in the desired area close to the application surface.

Larger quantities of fluid may be dispensed from large, complex reusable dispensers having a plurality of molded components. However, such dispensers are complex to manufacture and are not suitable for disposable single use applications. These rigid applicators are also difficult to control, such that a user may be unable to easily manipulate the substance flow rate.

Accordingly, there is an unmet need for a substance applicator system that holds and dispenses large quantities of substance. Moreover, there is an unmet need for an applicator head assembly for use with a substance applicator system that provides more control of the substance flow onto a desired surface.

BRIEF SUMMARY

Various embodiments are directed to an applicator for storing and dispensing a substance, wherein the applicator comprises a substance reservoir, a flexible support card, and an applicator head. The substance reservoir is configured for storing a substance therein, such as an antimicrobial drug or a cleaning substance, and comprises the flexible support card. The flexible support card comprises a closed score line defining an axis of rotation and is configured to flex about the axis of rotation between a closed configuration and an activated configuration in which the score line is opened when flexed. In various embodiments, the applicator head comprises a plurality of pores and is coupled to a surface of the flexible support card adjacent the score line. The applicator head is configured to flex with the flexible support card between the closed configuration in which at least a portion of the pores are compressed and an activated configuration in which at least a portion of the pores become less compressed when the flexible support card is flexed about the axis of rotation. In various embodiments the applicator head comprises a sponge, a foam material (e.g., polyurethane foam), a nonwoven material, and/or a woven material compressed and/or biased in a direction perpendicular to the axis of rotation to define the closed configuration. In various embodiments the applicator head comprises a sponge, a foam material (e.g., a polyurethane foam), a nonwoven material, and/or a woven material flexed such that at least a portion of the pores are compressed to define the closed configuration, and the sponge is uncompressed when the flexible support card is flexed about the axis of rotation to define an included angle between 0-180 degrees.

Moreover, in various embodiments the substance reservoir is configured to direct substance into the sponge when the flexible support card is opened, and the sponge is configured to change to the activated configuration upon receipt of the substance therein. In various embodiments, the substance reservoir is configured to direct the substance into the applicator head at a flow rate between one-twentieth of the volume of the substance reservoir per second and one-third of the volume of the substance reservoir per second when a 3 Newton force is applied to flex the flexible card.

Various embodiments are directed to an applicator for storing and dispensing a substance, wherein the applicator comprises a substance reservoir, a flexible support card, and an applicator head. The substance reservoir is configured for storing a substance therein, such as an antimicrobial drug or a cleaning substance, and comprises the flexible support card. The flexible support card comprises a closed score line defining an axis of rotation and is configured to flex about the axis of rotation between a closed configuration and an activated configuration in which the score line is opened when flexed. In various embodiments, the applicator head comprises a plurality of pores and defines a relief channel. The applicator head may be coupled to a surface of the flexible support card such that the relief channel is adjacent and parallel to the score line The applicator head is configured to flex with the flexible support card between the closed configuration in which at least a portion of the pores are compressed and an activated configuration in which at least a portion of the pores become less compressed when the flexible support card is flexed about the axis of rotation. Moreover, in various embodiments the applicator head defines at least two portions of the applicator head. The first portion has a first modulus of elasticity and is configured to be secured to the surface of the flexible card, and the second portion is adjacent to the first portion and spaced away from the flexible card and has a second modulus of elasticity that is less than the first modulus of elasticity. In various embodiments the applicator head comprises a sponge, a foam material (e.g., polyurethane foam), a nonwoven material, and/or a woven material compressed and/or biased in a direction perpendicular to the axis of rotation to define the closed configuration.

Various embodiments are directed to a method of dispensing a substance from a substance applicator. In various embodiments the method comprises rupturing a flexible card comprising a substance reservoir to form a channel through the flexible card between the substance reservoir and an applicator head by flexing the flexible card along a fold line. The method may additionally comprise steps for folding the flexible card along the fold line such that the substance is directed through the channel from the substance reservoir and into the applicator head, and expanding the applicator head such that at least a portion of the substance is directed through the applicator head to an application surface of the applicator head and is stored within the applicator head. The substance may then be applied to a target surface from an application surface of the applicator head.

BRIEF DESCRIPTION OF THE SEVERAL VIEWS OF THE DRAWINGS

Reference will now be made to the accompanying drawings, which are not necessarily drawn to scale, and wherein:

FIG. 14 is a schematic diagram illustrating a process for manufacturing an applicator head according to various embodiments.

DETAILED DESCRIPTION

Figure 1:
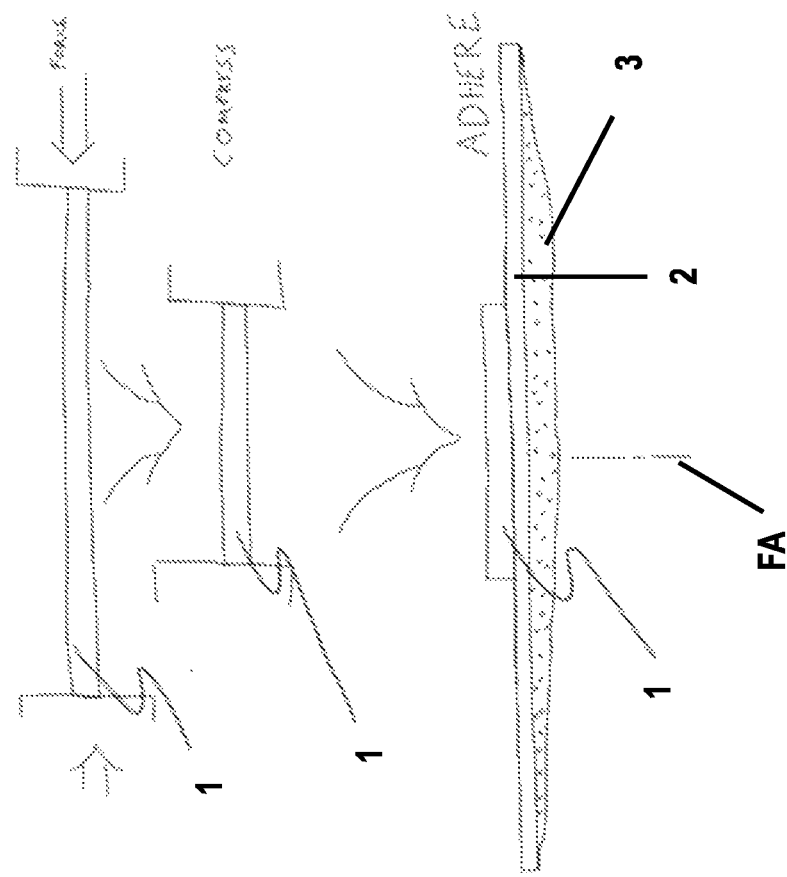
FIG. 1 is a schematic diagram illustrating compression of an applicator head according to various embodiments.

The present invention will now be described more fully hereinafter with reference to the accompanying drawings, in which some, but not all embodiments of the invention are shown. Indeed, the invention may be embodied in many different forms and should not be construed as limited to the embodiments set forth herein. Rather, these embodiments are provided so that this disclosure will satisfy applicable legal requirements. Like numbers refer to like elements throughout.

Various embodiments are directed to an applicator for loading, meting, or otherwise dispensing a substance in a controlled manner having an applicator head secured to a flexible card, wherein the flexible card comprises a flexible substance reservoir having an amount of substance stored therein. The applicator may be used to apply substances to skin (e.g., cosmetics, cleaners, oils, and/or the like) or other target surfaces.

The substance reservoir is configured to open and provide substance to the applicator head upon flexing and rupturing the flexible card along a fold axis, which may comprise a score line configured to rupture upon folding the flexible card along the fold line. The flow rate of substance into the applicator head may thereafter be manipulated by changing the amount of force provided to flex the flexible card, thereby compressing the substance reservoir and directing substance into the applicator head.

The applicator head may comprise a porous material (e.g., an open-cell foam, a sponge, a felt material, a woven material, a pulp material, a pulp derivative material, a cotton material, a silk material, a fiber material, and/or the like) having at least substantially uniform pore sizes throughout the material configured such that the substance may flow through the applicator head to an applicator surface opposite the flexible card. Moreover, in various embodiments the applicator head comprises a gradient of pore sizes throughout the material. For example, the applicator head may comprise a tubular structure having a plurality of pores defining at least substantially parallel channels forming a honeycomb structure. For example, the applicator head may comprise any of a plurality of materials demonstrating flowing and buffering properties. For example, as a substance is introduced to the applicator head, the applicator head may be configured to absorb at least a portion of the substance and thereby provide a substance buffer as the substance is being applied to a surface and thereby impede dripping of the substance. As a non-limiting example, the volume of the applicator head may be at least 10% of the volume of substance stored within the substance reservoir, and less than 200% of the volume of the substance stored within the substance reservoir, such that at least a portion of the substance may be absorbed and stored within the applicator head during dispensing. Moreover, the applicator head may be flexible such that the applicator head may conform to a surface while the substance is being applied to the surface.

The applicator may be configured to apply any of a variety of substances to a surface. For example, such substances may comprise one or more of liquids, semi-liquids, low viscosity liquids, high viscosity liquids (e.g., lipids and/or oils), powders, cleaning agents, dyes, coloring agents, antimicrobial drugs, reactants, reagents (e.g., acids and/or bases), thermal reactants, light emitting reactants, epoxies, adhesives, and/or the like. As non-limiting examples, such substances may comprise surgical preparation solutions for use in sanitizing a surface prior to a surgical procedure, cosmetics, adhesives, and/or the like.

In various embodiments, at least a portion of the applicator head is compressed (e.g., deformed, distorted, pre-stressed, and/or shaped) to create a recess in the applicator head proximate the channel through the flexible card between the fluid reservoir and the applicator head via physical, thermal, and/or chemical compression, such that the pores of the applicator head are compressed. In various embodiments, portions of the applicator head are compressed so as to facilitate increased fluid flow in certain areas and decreased fluid flow in other areas of the applicator head. For example, the applicator head may be compressed by collapsing the pores of the applicator head between two surfaces (e.g., physical compression). As another example, the applicator head may be compressed by exposing the applicator head to high or low temperatures such that the applicator head contracts and the pores of the applicator head are compressed. As yet another example, the applicator head may be compressed by applying a chemical to the applicator head which causes the applicator head to contract and thereby compress the pores of the applicator head. As yet another example, a portion of the applicator head may be compressed by bending (e.g. rotating) the applicator head about an axis of rotation, such that a portion of the pores of the applicator head proximate the interior surface of the bend are compressed, and a portion of the pores proximate the opposite, exterior surface of the bend are stretched under tension. Thus, at least a portion of the applicator head is compressed by flexing the applicator head about an axis of rotation in a direction opposite the expected rotation of the applicator head and associated flexible card upon activation of the applicator.

The applicator head may be biased in the compressed state, such that the applicator head will not return to the uncompressed state without application of a substance (e.g., the substance stored within the substance reservoir) and/or an external force. Various embodiments of the applicator head are biased by annealing the applicator head after compressing the applicator head. Such annealing may comprise exposing the applicator head to mechanical compression and/or thermal compression (e.g., by applying heat) such that the applicator head does not return to its original size and shape after annealing and is instead biased to the compressed size and shape. Biasing the applicator head may reduce the amount of strain on the attachment mechanism used to attach the applicator head to the flexible card as compared to a compressed and unbiased applicator head. For example, whereas a compressed and unbiased applicator head is maintained in the compressed position by the attachment mechanism utilized to secure the applicator head to the flexible card, a compressed and biased applicator head may maintain the compressed configuration without application of an external force.

Moreover, in various embodiments, exposing the applicator head to heat may cause the applicator head to contract in size and thereby compress pores therein. For example, an applicator head comprising two component fibers (e.g., side-by-side polypropylene, polyethylene, polyester, rayon, and/or the like) may contract and thereby compress the pores therein without mechanical compression.

In various embodiments, upon directing the substance into the applicator head, at least a portion of the applicator head expands to the original, decompressed form, thereby decompressing the various pores, and directing the substance to the applicator surface of the applicator head. As the applicator head decompresses, the pores and/or channels extending through the applicator head reopen such that the substance may flow through the applicator head. Moreover, in various embodiments the applicator head may be configured such that, after a substance is introduced to the applicator head, at least the portion of the applicator head proximate the channel through the flexible card between the substance reservoir and the applicator head expands to substantially its original size and shape.

Referring first to FIG. 1, which is a schematic diagram illustrating compression of an applicator head according to various embodiments, the applicator may comprise an applicator head 1, a flexible card 2, and a substance reservoir 3. In the illustrated embodiment of FIG. 1, the applicator head 1 comprises a flexible porous material (e.g., a foam). Moreover, the flexible card 2 may comprise a plastic material, a metal material, organic or inorganic materials, paper material, cardboard material, and/or the like. The substance reservoir 3 may comprise a flexible pouch secured to the flexible card 2. As a non-limiting example, the substance reservoir 3 may comprise a flexible plastic sheet having each side secured to a side of the flexible card such that collectively the flexible card 2 and the plastic sheet form an enclosed volume. As yet another example, the flexible card 2 may comprise a plurality of individual laminated layers, wherein the substance reservoir 3 is formed between two of the laminated layers. In various embodiments, the substance reservoir 3 is configured such that various substances may be stored therein and directed into the applicator head 1. Moreover, as non-limiting examples, the substance reservoir 3 may have a volume between 0.5 mL and 17 mL. As non-limiting examples, the substance may comprise a fluid (e.g., a fluid having a specific gravity between 0.15-2.40 and a viscosity between 0.5 mPa-s-1000 cps), a fine powder, and/or the like.

Referring again to FIG. 1, the applicator head 1 may be compressed in a direction perpendicular to the fold axis FA and along a plane parallel to a flexible card 2 prior to attachment to the flexible card 2. In various embodiments, the applicator head is held in the compressed shape by applying a backing and/or an adhesive configured to hold the applicator head 1 in its compressed shape.

In the illustrated embodiment of FIG. 1, the applicator head 1 is secured to a surface of the flexible card 2 to ensure the applicator head 1 does not relax to its original state. As non-limiting examples, the applicator head is compressed by a factor of at least 1.2 and less than 5. When the applicator is activated for use and the card is folded along the fold axis FA, at least a portion of the applicator head 1 expands and thus recovers at least some of its original shape. This reduced distortion may allow the fluid to flow through the applicator head 1 at a desired flow rate as a user is applying a force to fold the flexible card 2. As the applicator head 1 expands, the applicator head 1 absorbs a portion of the substance being directed out of the fluid reservoir 3, thereby reducing the risk of pooling or dripping. Moreover, the reduced compression during dispensing may provide a soft, conformable applicator head 1 that may facilitate uniform distribution of a substance on a non-uniform surface (e.g., skin).

Figure 2:
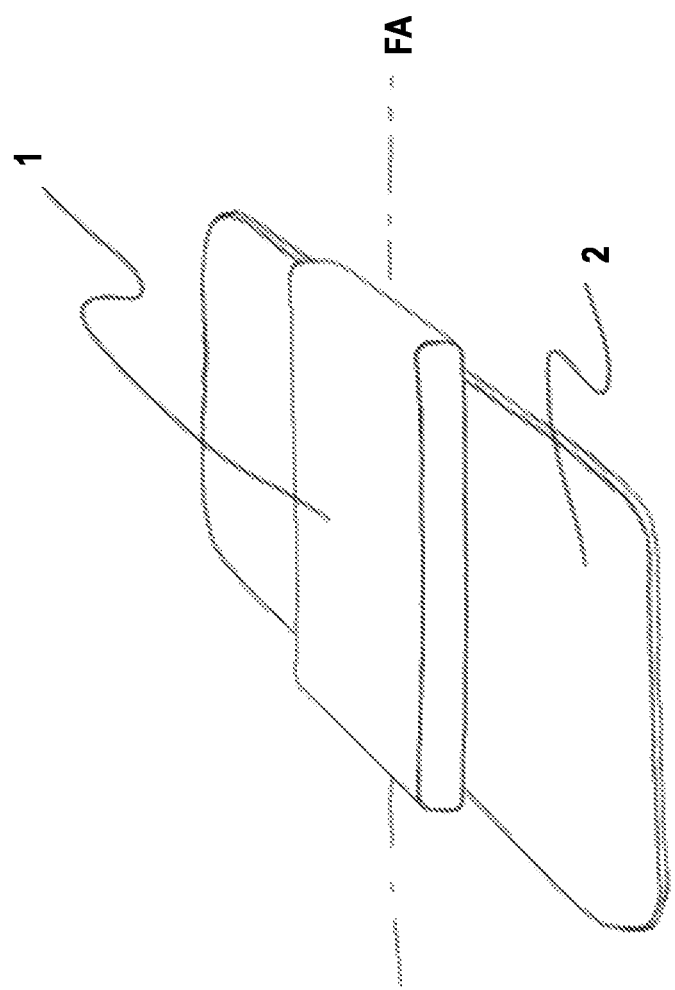
FIG. 2 is a schematic diagram illustrating a perspective view of an applicator according to various embodiments.
Figure 3:
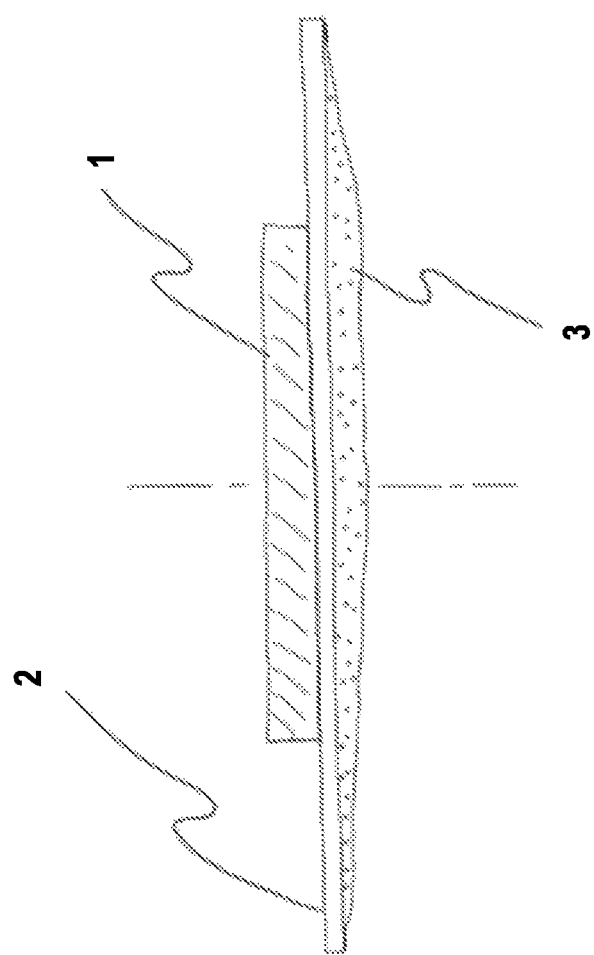
FIG. 3 is a schematic diagram illustrating a cross-sectional view of an applicator according to various embodiments.

As shown in FIGS. 2 and 3, which are schematic diagrams of an applicator according to various embodiments, the applicator head 1 may be secured to a surface of the flexible card 2 proximate the fold axis FA, such that, as the flexible card ruptures along the fold axis FA to form a channel between the substance reservoir 3 and the applicator head 1, substance is directed into the applicator head 1. Specifically as shown in FIG. 3, which is a cross sectional view of the applicator along a plane extending along the length of the applicator perpendicular to the fold axis FA, prior to activation, the substance reservoir 3 is sealed, such that there is no path from the substance reservoir 3 to the applicator head 1.

In various embodiments, the applicator head 1 is compressed by physically compressing the applicator head 1 in a direction perpendicular to the fold axis FA and along a plane parallel to the flexible card 2. In various embodiments, the applicator head 1 is annealed such that the applicator head 1 is biased to the compressed form. Such annealing may comprise exposing the applicator head 1 to heat or low temperatures, applying a chemical reagent to the applicator head 1, and/or the like. The compressed applicator head 1 is then secured to the surface of the flexible card 2. For example, the applicator head 1 may be secured to the flexible card via an adhesive (e.g., a glue or tape) such that substance may be directed from the substance reservoir 3 into the applicator head 2 via the channel formed along the fold axis FA. As additional non-limiting examples, the applicator head 1 may be secured to the flexible card 2 via one or more curing adhesives (e.g., epoxy resins, UV curing resins, cyanoacrylate type adhesives, other two-part or one-part curing adhesives), hotmelt adhesives, adhesive films, thermal welding, ultrasonic welding, overmolding, mechanical attachment (e.g., a cradle, harness, and/or the like). When the applicator is activated for use and card is folded along the fold axis FA, at least a portion of the applicator head 1 recovers some of its original shape, reducing compression and distortion. In various embodiments, this reduction in compression occurs proximate the fold axis FA.

As a non-limiting example, an applicator head 1 may comprise reticulated polyester polyurethane foam compressed in a direction perpendicular to the fold axis to between one-half and one-quarter of the original length and heated to anneal the foam and thereby bias the foam in the compressed configuration. The foam is then secured to the flexible card adjacent the score line.

Figure 4:
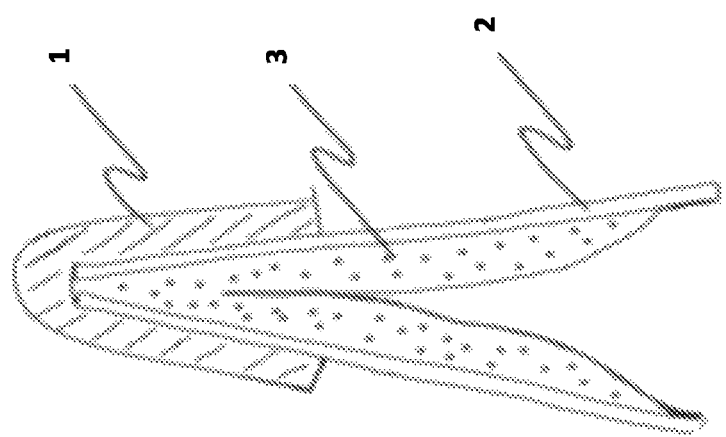
FIG. 4 is a schematic diagram illustrating a cross-sectional view of an activated applicator according to various embodiments.

FIG. 4 illustrates an applicator in activated form. As shown in FIG. 4, when the flexible card 2 is folded along the fold axis FA, the flexible card ruptures, such that the substance within the substance reservoir 3 may be directed into the applicator head 1. Although not shown in the Figures, the flexible card 2 may have a score line along the fold axis FA to facilitate bending and rupturing the flexible card 2 to form a channel between the substance reservoir 3 and the applicator head 1.

Figure 5:
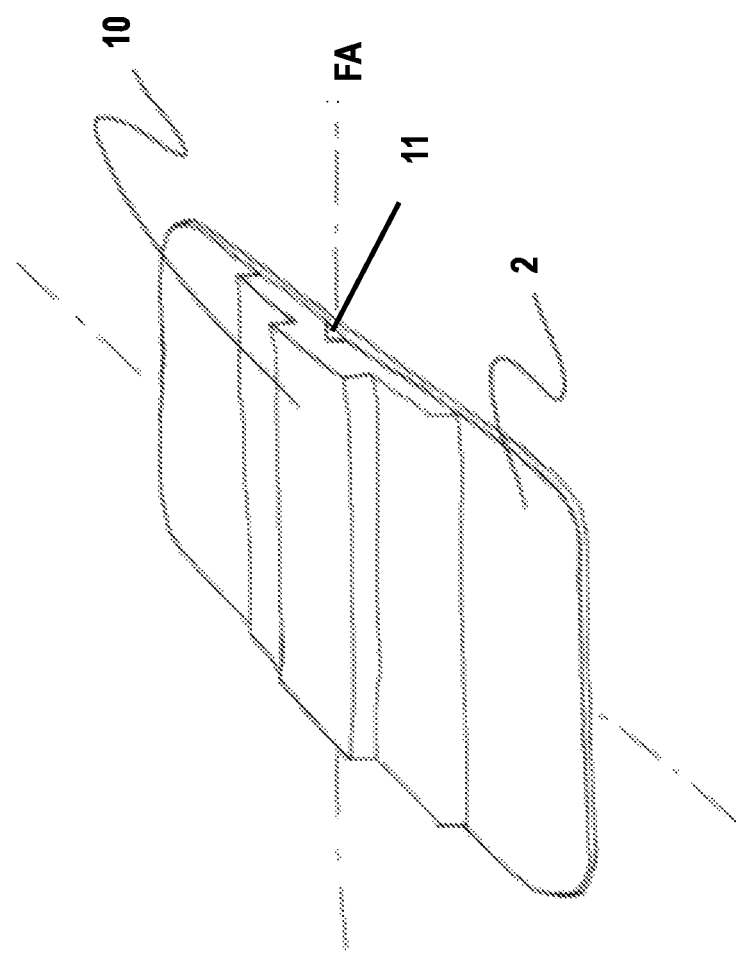
FIG. 5 is a schematic diagram illustrating a perspective view of an applicator having a relief channel according to various embodiments.
Figure 6:
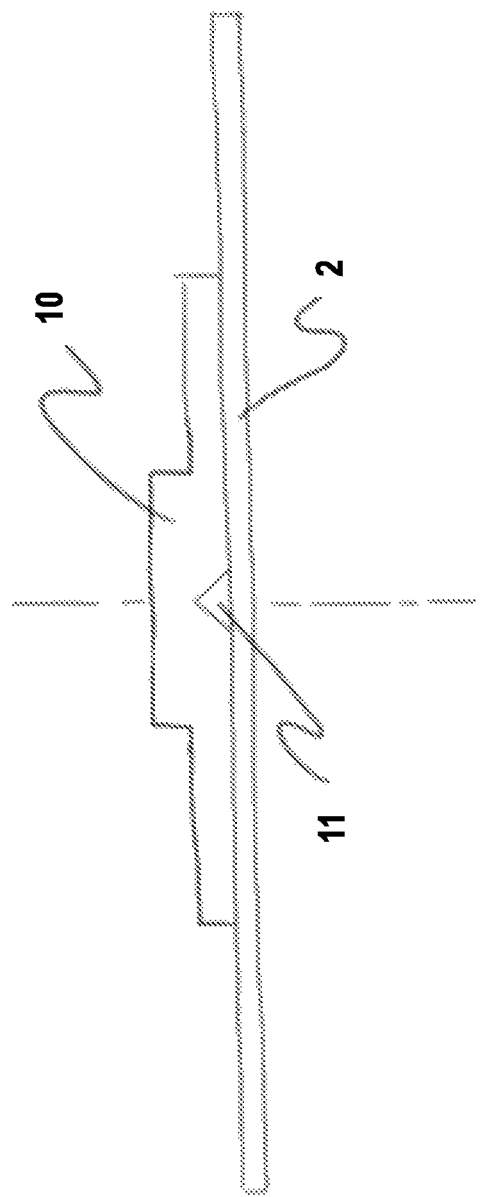
FIG. 6 is a schematic diagram illustrating a side view of an applicator having a relief channel according to various embodiments.

FIG. 5 illustrates a schematic diagram of an applicator according to various embodiments. As shown in FIG. 5, the applicator may comprise an applicator head 10, a flexible card 2, and a substance reservoir 3. As shown in FIG. 5, the applicator head 10 may comprise a relief channel 11 adjacent a fold axis FA of the flexible card 2 to facilitate folding the flexible card 2. In various embodiments, the relief channel 11 extends across the width of the applicator head 10. FIG. 6 illustrates a side view of the applicator according to various embodiments. As shown in FIG. 6, the relief channel 11 may comprise a "V"-shaped profile centered on the fold axis FA of the flexible card 2.

In various embodiments, the relief channel 11 may be configured to facilitate bending of the applicator head 10. Moreover, in various embodiments, the applicator head 10 may comprise a plurality of portions of applicator head material each having a different modulus of elasticity. For example, the modulus of elasticity in the portion proximate the flexible card 2 may be higher than the modulus of elasticity of the portion proximate the applicator surface. In various embodiments, the modulus of elasticity of the portion proximate the flexible card 2 is substantially double the modulus of elasticity of the portion of the applicator head proximate the applicator surface.

Figure 7:
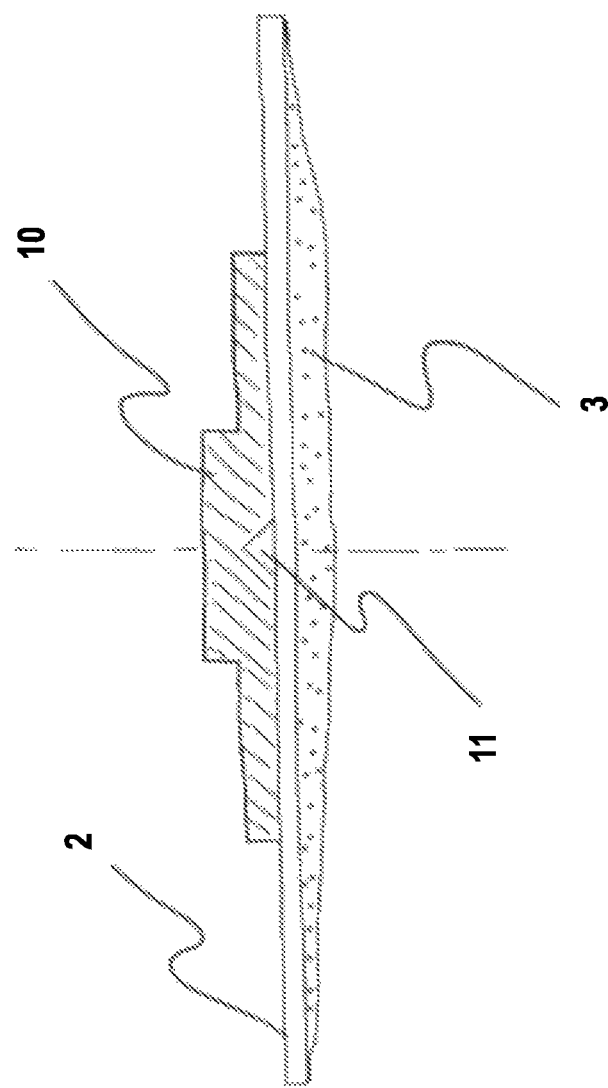
FIG. 7 is a schematic diagram illustrating a cross-sectional view of an applicator having a relief channel according to various embodiments.

FIG. 7 illustrates a cross sectional view of the applicator along a plane perpendicular to the fold axis FA. As shown in FIG. 7, prior to folding the flexible card 2 along the fold axis FA, the substance reservoir 3 is sealed such that substance cannot move from the substance reservoir into the applicator head 10.

Figure 8:
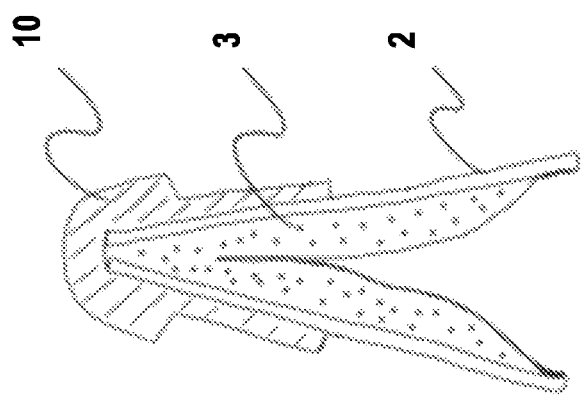
FIG. 8 is a schematic diagram illustrating a cross-sectional view of an activated applicator having a relief channel according to various embodiments.

Once the flexible card is folded along the fold axis FA as shown in FIG. 8, the flexible card ruptures along the fold axis FA to form a channel between the substance reservoir 3 and the applicator head 10 and substance may be directed from the substance reservoir 3 into the applicator head 10.

Figure 9:
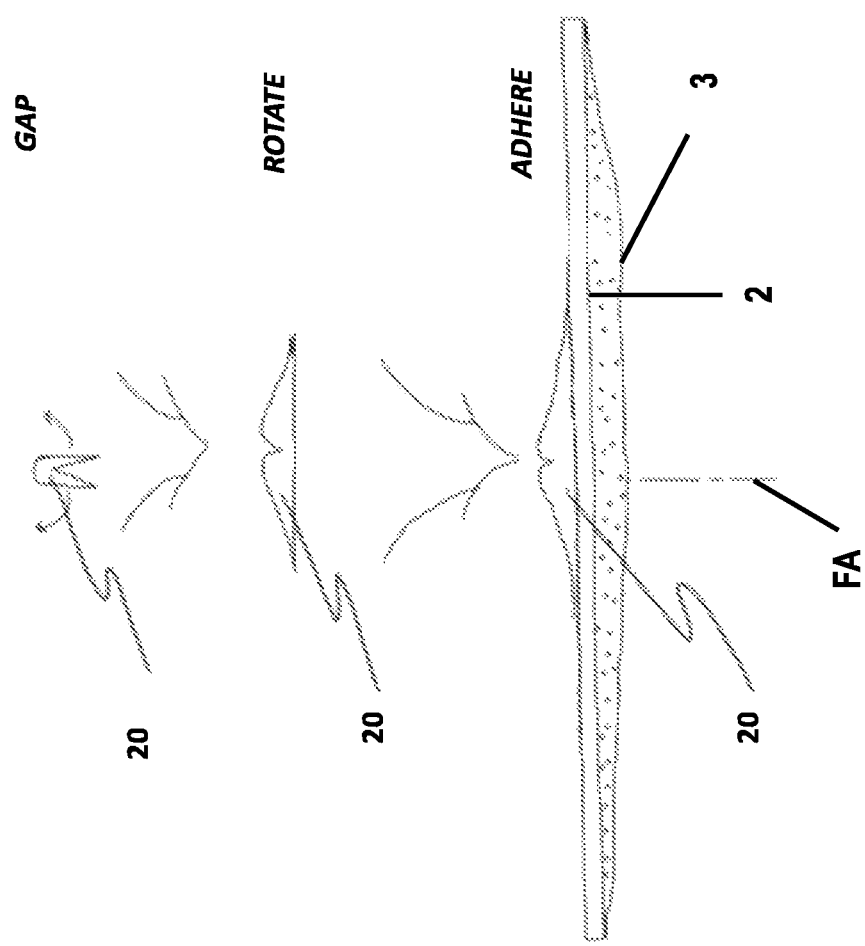
FIG. 9 is a schematic diagram illustrating rotational compression of an applicator head according to various embodiments.

FIG. 9 illustrates a schematic diagram of various steps for providing physical compression to an applicator head 20 according to various embodiments. As shown in FIG. 9, the applicator head 20 may have a bottom surface defining a bottom channel defined by two lower edges prior to compression. In various embodiments, the bottom channel may have a "V"-shape, wherein each of the two surfaces of the channel surface are oriented at an angle relative to one another. As a non-limiting example, the angle between the surfaces of the channel surface may comprise an angle between 90 degrees and 180 degrees.

Compression may comprise rotating the two lower edges away from each other to form a substantially flat bottom surface comprising the channel surface. In various embodiments, the axis of rotation for compressing the applicator head 20 may be within the applicator head 20 or within 30 mm of the applicator head (e.g., such that the axis of rotation aligns with the fold axis FA of the flexible card). The top surface of the applicator head 20 is thus compressed, and the bottom surface is placed under tension. In various embodiments in which the applicator head 1 comprises a porous material, the pores of the applicator head are deformed, such that those pores proximate the upper surface of the applicator head 20 are compressed and those pores proximate the lower surface of the applicator head 20 are stretched.

Referring again to FIG. 9, the compressed applicator head 20 is secured to the flexible card 2 such that the bottom surface of the applicator head 20 is secured to a surface of the flexible card 2 opposite the substance reservoir 3. Upon flexing the flexible card 2 along the fold axis FA, the flexible card ruptures along the fold axis FA to form a channel between the substance reservoir 3 and the applicator head 20 and the applicator head 20 is flexed in the direction opposite the original compression rotation direction and toward a decompressed form. For example, the applicator head 20 is flexed such that the bottom surface of the applicator head 20 forms a channel surface. In various embodiments, the applicator head 20 is in an uncompressed configuration when the flexible card 2 with the applicator head 20 secured thereto is flexed about the fold axis FA to define an included angle between 0-180 degrees between the portions of the flexible card 2 adjacent the fold axis FA. For example, the applicator head 20 is in an uncompressed configuration when the flexible card 2 with the applicator head 20 secured thereto is flexed about the fold axis FA such that the included angle between each portion of the flexible card 2 adjacent the fold axis FA is between 0-180 degrees. As an additional non-limiting example, the applicator head 20 is in an uncompressed configuration when the flexible card 2 with the applicator head 20 secured thereto is flexed about the fold axis FA such that the included angle between each portion of the flexible card 2 adjacent the fold axis FA is between 0-90 degrees. The pores of the applicator head 20 may be relaxed, such that substance may flow from the substance reservoir 3 to the top surface of the applicator head 20. Moreover, the pores of the applicator head 20 may be configured to absorb at least a portion of the substance to impede dripping or pooling of the substance. Moreover, the reduced compression of the applicator head 20 during dispensing forms a softer, conformable applicator head that may facilitate uniform application of a substance to a non-uniform surface (e.g., skin).

Figure 10:
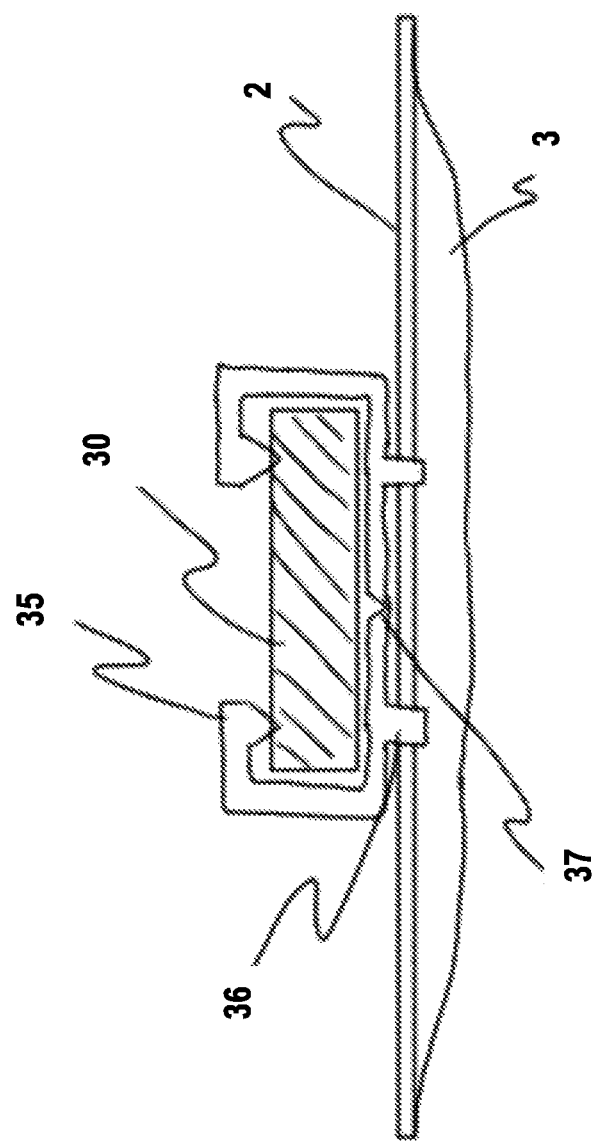
FIG. 10 is a schematic diagram of a side view of an applicator having an applicator head attachment according to various embodiments.

FIG. 10 is a schematic diagram of an applicator according to various embodiments. As shown in FIG. 10, the applicator may comprise an applicator head 30, a head frame 35, a flexible card 2, and a substance reservoir 3. Thus, the flexible card 2 may comprise a plastic card, a metal card, and/or the like. Moreover, the substance reservoir 3 may comprise a plastic sheet secured to the flexible card 2 such that collectively the flexible card 2 and the substance reservoir 3 define an interior volume.

As shown in FIG. 10, the applicator head 30 may be secured to the flexible card 2 via the head frame 35. The head frame 35 may thus define an interior portion configured to support the applicator head 30. In various embodiments, the applicator head 30 is compressed and/or annealed similar to applicator head 1 (e.g., via physical compression, thermal compression, chemical compression, and/or the like).

Moreover, as shown in FIG. 10, the head frame 35 is secured to the flexible card 2 via one or more frame clips 36. Moreover, although not shown, the head frame 35 may be secured to the flexible card 2 via an adhesive (e.g., glue, tape, and/or the like). The head frame illustrated in FIG. 10 comprises one or more hinges 37 each configured to flex or break upon bending of the flexible card 2, located proximate the fold axis FA of the flexible card 2. Thus, as the flexible card 2 is flexed along the fold axis FA such that the flexible card 2 ruptures to form a channel between the substance reservoir 3 and the applicator head 30, the head frame 35 is configured to flex via the one or more hinges 37.

Figure 11:
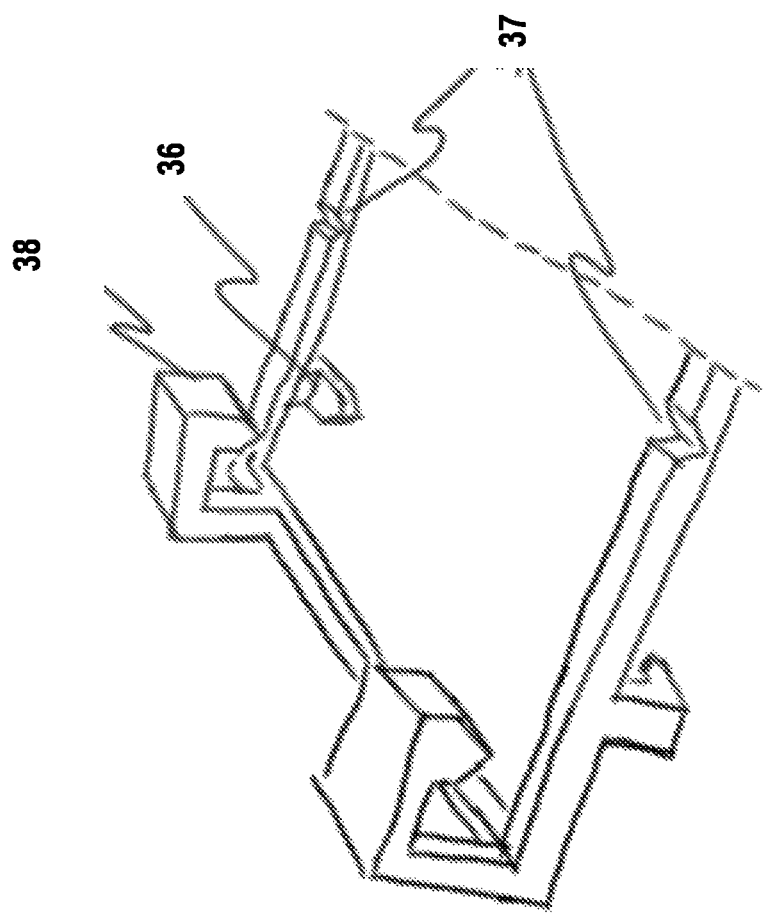
FIG. 11 is a schematic diagram of a partial perspective view of an applicator head attachment according to various embodiments.

FIG. 11 is a perspective view of a portion of the head frame 35. As shown in FIG. 11, the head frame 35 comprises one or more applicator head fasteners 38. In various embodiments, the applicator head fasteners comprise overhanging portions having engagement features (e.g., spikes) configured to engage and secure a top surface of the applicator head 30.

Figure 12:
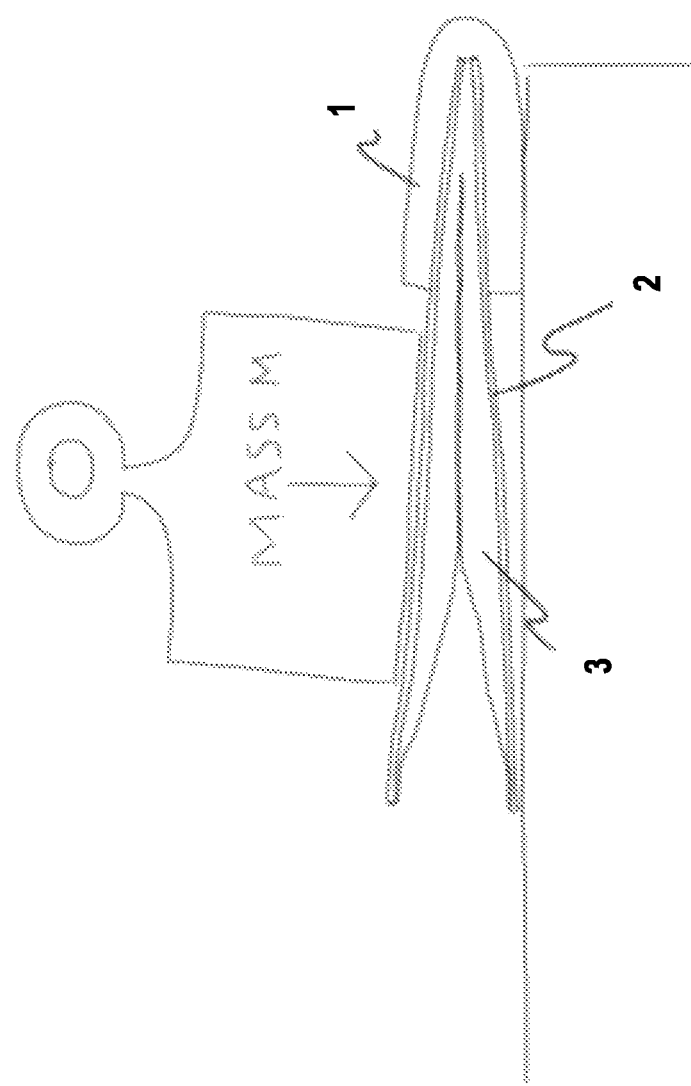
FIG. 12 is a schematic diagram of an activated applicator according to various embodiments.

FIG. 12 illustrates an applicator in an activated state. As shown in FIG. 12, a mass may be applied to flex the flexible card 2 along the fold axis FA, thereby compressing the substance reservoir 3. As shown in FIG. 12, the flexible card 2 is ruptured along the fold axis FA to form a channel between the substance reservoir 3 and the applicator head 1, thus the substance is directed out of the substance reservoir 3 and into the applicator head 1 as a force is applied to flex the flexible card 2. For example, the flexible card 2 may be configured to flex and rupture upon application of a force by two fingers of a user. After rupturing, the flexible card 2 may be configured to flex and thereby direct the substance into the applicator head 1 and to the applicator surface upon the application of a force between 0.1 Newtons and 50 Newtons, and more preferably between 0.5 Newtons and 10 Newtons. In various embodiments, the flow rate of the substance out of the substance reservoir 3 may be directly proportional to the amount of force applied to flex the flexible card. Thus, the flow rate of the fluid out of the fluid reservoir may increase as the amount of force applied to the flexible card 2 is increased. Thus, a user may control the flow rate of the substance by varying the amount of force applied to flex the flexible card 2. As a non-limiting example, by varying the amount of force applied to the flexible card, the flow rate may be controlled between approximately 1/20 of the total substance reservoir volume per second to approximately 1/3 of the total substance reservoir volume per second. As the substance is being directed into the applicator head 2, a user may wipe the applicator head against a surface to apply the substance to the surface.

In various embodiments, the flow rate of the applicator may be measured by applying a known force to flex the applicator while the applicator is resting on a flat, horizontal surface as shown in FIG. 12. The known force may be applied by placing an object having a known mass on the flexible card 2. The flow rate may then be determined by measuring the amount of time necessary to at least substantially drain the substance reservoir. Utilizing a known amount of substance, the flow rate may be determined by dividing the amount of substance within the substance reservoir 3 by the amount of time needed to drain the substance reservoir 3.

As yet another method for determining the flow rate of the substance, a known force may be applied to the applicator while resting on a flat, horizontal surface as shown in FIG. 12. The known force may be applied by placing an object having a known mass on the flexible card 2 for a predetermined amount of time (e.g., 10 seconds). After the predetermined time has elapsed, the remaining substance in the substance reservoir is drained (e.g., via an incision in the fluid reservoir). The flow rate of the substance is determined by determining the difference between the initial fluid volume and the final fluid volume (as determined by the amount of fluid that was drained from the fluid reservoir), divided by the predetermined amount of time.

As an example, consider a flexible card having a 15 mL substance reservoir with a reticulated polyester foam applicator head which has been thermally set to half its height. The substance reservoir is filled with a 70% isopropyl alcohol, 30% water formulation for use as a surgical preparation solution. The flexible card is folded to rupture the card and thereby initiate substance dispensing. A constant force of 3 N is applied to the flexible card for 10 seconds and then removed. A total of 10 mL is evacuated from the reservoir into the applicator head to the applicator surface. This is ascertained since the remaining liquid in the reservoir when drained after the 10 second dispensing period is 5 ml. In this case the average fluid flow-rate is approximately 1 ml/s (calculated by Fluid flowrate average={Initial volume−final volume}/Time of flow={15 ml−5 ml}/10 s=1 ml/s. In this case of a 3 N force the flow-rate can be described as 1/10 of the total package volume per second. A similar applicator is subjected to a 2 N force on the reservoir and the resulting flow is approximately 0.5 ml/s, illustrating that the fluid flow rate may be controlled by varying the amount of force applied to flex the flexible card.

Figure 13:
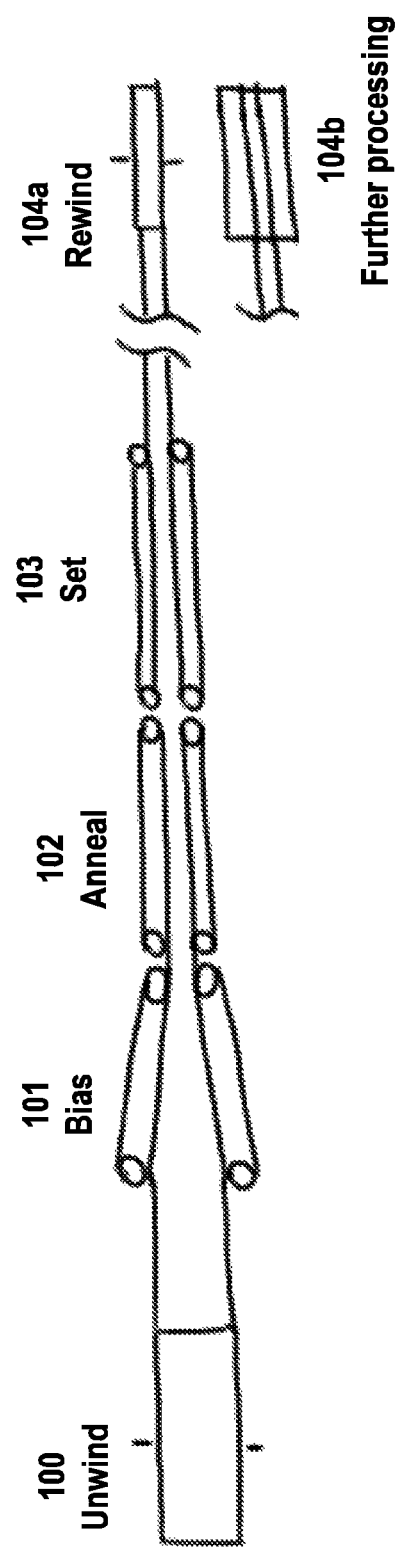
FIG. 13 is a schematic diagram illustrating a process for manufacturing an applicator head according to various embodiments.

FIGS. 13 and 14 illustrate exemplary steps for manufacturing an applicator head according to various embodiments. As shown in FIG. 13, the applicator head material may be provided on a source roll. The applicator head material may be unwound from the source roll at step 100. The applicator head material is biased at step 101 by mechanically compressing the applicator head material. For example, the applicator head material may be biased by compressing the applicator head material between belts, rollers, press plates, and/or the like. At step 102 the applicator head material is annealed (e.g., via thermal and or chemical annealing). For example, during annealing 102, heat may be applied to the applicator head material, before the applicator head material is cooled. As shown in FIG. 13, at step 103 the applicator head material is set such that the material is biased to the compressed form. In various embodiments, the biasing and annealing steps 101, 102 may occur concurrently. Moreover, in various embodiments, setting 103 may occur by applying a chemical agent and/or adhesive to the material to set the material in the biased form.

After the applicator head material is biased and set via steps 101-103, the applicator head material may be wound onto a take-up spool at step 104a, or may be provided to additional processing mechanisms for additional in-line processing at step 104b. For example, the applicator head material may be provided to additional mechanisms for manufacturing individual applicator head portions to be secured to individual flexible cards.

As shown in FIG. 14, the applicator head material may be provided on a source roll. The applicator head material may be unwound from the source roll at step 200. The applicator head material is compressed at step 201 by mechanically compressing the applicator head material. For example, the applicator head material may be compressed between belts, rollers, press plates, and/or the like. At step 202 a chemical is applied to the applicator head material. For example, an adhesive is applied to the applicator head material to anneal and bias the applicator head material to the compressed configuration. In various embodiments, step 202 may additionally comprise thermal annealing. For example, heat may be applied to the applicator head material, before the applicator head material is cooled. As shown in FIG. 14, at step 203 the chemical (e.g., adhesive) is set (e.g., cooled and/or cured) such that the applicator head material is biased to the compressed configuration.

After the applicator head material is biased and set via steps 201-203, the applicator head material may be wound onto a take-up spool at step 204a, or may be provided to additional processing mechanisms for additional in-line processing at step 204b. For example, the applicator head material may be provided to additional mechanisms for manufacturing individual applicator head portions to be secured to individual flexible cards.

Such manufacturing processes may be performed at least substantially continuously (e.g., by providing a continuous roll of applicator head material the manufacturing steps) and/or may be performed in one or more batches each comprising a predefined amount of applicator head material.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

For example, the applicator head may comprise a layered structure comprising one or more materials bonded together. For example, such materials may comprise sponges, nonwoven materials, films, and/or woven materials bonded together to create a layered applicator head. Moreover, the applicator head may comprise materials, in layered or non-layered form, such as papers, gauzes, textiles, cotton, wool, microfibers, nano-fibers, spunbond fibers, meltblown fibers, and/or the like. Moreover, in various embodiments, a foam or sponge material may comprise an organic or inorganic material, such as open cell materials, polypropylene materials, polyethylene materials, reticulated materials, viscoelastic materials, neoprene, sorbothane, and/or the like.

Moreover, the applicator head may comprise a surface layer or coating on the applicator surface. As a non-limiting example, the application head may comprise an abrasive (e.g., melamine fibers), and/or a micro-textured coating to facilitate even distribution of substance on a surface.

That which is claimed:

1. An applicator for storing and dispensing a substance, the applicator comprising:
    a substance reservoir configured for storing a substance therein, wherein the substance reservoir comprises a flexible support card having at least one closed score line defining at least one axis of rotation and configured to flex about the at least one axis of rotation between a closed configuration and an activated configuration that opens the at least one score line when flexed; and
    an applicator head comprising a plurality of pores and coupled to a surface of the flexible support card adjacent the at least one score line, wherein the applicator head is configured to flex with the flexible support card between:
        the closed configuration in which at least a portion of the pores are compressed; and
        the activated configuration in which at least a portion of the pores become less compressed when the flexible support card is flexed about the axis of rotation; and
    wherein the substance reservoir is configured to direct the substance into the applicator head at a flow rate between one-twentieth of the volume of the substance reservoir per second and one-third of the volume of the substance reservoir per second when a 3 Newton force is applied to flex the flexible support card.

2. The applicator of claim 1, wherein the applicator head comprises a sponge compressed in a direction perpendicular to an axis of rotation to define the closed configuration.

3. The applicator of claim 2, wherein the sponge is biased to the closed configuration.

4. The applicator of claim 3, wherein the substance reservoir is configured to direct substance into the sponge when the flexible support card is opened, and the sponge is configured to change to the activated configuration upon receipt of substance therein.

5. The applicator of claim 2, wherein the applicator head comprises a sponge flexed such that at least a portion of the pores are compressed to define the closed configuration.

6. The applicator of claim 5, wherein the sponge is in an uncompressed configuration when the flexible support card is flexed about the axis of rotation to define an included angle between 0-180 degrees.

7. The applicator of claim 1, wherein the substance comprises at least one of an antimicrobial drug or a cleaning substance.

8. The applicator of claim 1, wherein the applicator head comprises at least one of: a foam material, a nonwoven material, or a woven material.

9. The applicator of claim 8, wherein the applicator head comprises a polyurethane foam.

10. An applicator for storing and dispensing a substance, the applicator comprising:
    a substance reservoir configured for storing a substance therein, wherein the substance reservoir comprises a flexible support card having a closed score line defining an axis of rotation and configured to flex about the axis of rotation between a closed configuration and an activated configuration that opens the score line; and an applicator head comprising a plurality of pores and defining at least in part a relief channel and coupled to a surface of the flexible support card such that the relief channel is adjacent and parallel to the score line, wherein the applicator head is configured to flex with the flexible support card between:
  the closed configuration in which at least a portion of the pores are compressed; and
  the activated configuration in which at least a portion of the pores become less compressed when the flexible support card is flexed about the axis of rotation; and
wherein the applicator head defines a first portion and a second portion adjacent the first portion, the first portion having a first modulus of elasticity and being configured to be secured to the surface of the flexible card, and the second portion having a second modulus of elasticity, wherein the first modulus of elasticity is greater than the second modulus of elasticity.

11. The applicator of claim 10, wherein the applicator head comprises a sponge compressed in a direction perpendicular to the axis of rotation to define the closed configuration.

12. The applicator of claim 11, wherein the sponge is biased to the closed configuration.

13. The applicator of claim 12, wherein the substance reservoir is configured to direct substance into the sponge when the flexible support card is opened, and the sponge is configured to change to the activated configuration upon receipt of substance therein.

14. The applicator of claim 10, wherein the substance comprises at least one of an antimicrobial drug or a cleaning substance.

15. The applicator of claim 10, wherein the substance reservoir is configured to direct the substance into the applicator head at a flow rate between one-twentieth of the volume of the substance reservoir per second and one-third of the volume of the substance reservoir per second when a 3 Newton force is applied to flex the flexible support card.

16. The applicator of claim 10, wherein the applicator head comprises at least one of: a foam material, a nonwoven material, or a woven material.

17. The applicator of claim 16, wherein the applicator head comprises a polyurethane foam.

* * * * *